United States Patent
Morikawa et al.

(10) Patent No.: US 9,733,262 B2
(45) Date of Patent: Aug. 15, 2017

(54) METHOD FOR MEASURING BLOOD COAGULATION

(71) Applicant: SEKISUI MEDICAL CO., LTD., Chuo-ku (JP)

(72) Inventors: Chizuru Morikawa, Ryugasaki (JP); Remi Nakamura, Ryugasaki (JP); Mitsuaki Yamamoto, Ryugasaki (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 0 days.

(21) Appl. No.: 14/658,911

(22) Filed: Mar. 16, 2015

(65) Prior Publication Data

US 2015/0185236 A1 Jul. 2, 2015

Related U.S. Application Data (60) Continuation of application No. 14/153,739, filed on Jan. 13, 2014, now abandoned, which is a division of application No. 13/321,732, filed as application No. PCT/JP2010/003401 on May 20, 2010, now abandoned.

(30) Foreign Application Priority Data

May 20, 2009 (JP) ................................ 2009-121834

(51) Int. Cl.
| | | |
|---|---|---|
| *G01N 33/86* | (2006.01) | |
| *A61K 31/155* | (2006.01) | |
| *C07C 279/02* | (2006.01) | |
| *C07C 279/14* | (2006.01) | |
| *C07C 281/16* | (2006.01) | |
| *C12Q 1/56* | (2006.01) | |

(52) U.S. Cl.
CPC ........... *G01N 33/86* (2013.01); *A61K 31/155* (2013.01); *C07C 279/02* (2013.01); *C07C 279/14* (2013.01); *C07C 281/16* (2013.01); *C12Q 1/56* (2013.01)

(58) Field of Classification Search
None
See application file for complete search history.

(56) References Cited

U.S. PATENT DOCUMENTS

| | | | |
|---|---|---|---|
| 5,358,853 A | 10/1994 | Butler et al. | |
| 5,401,663 A | 3/1995 | Yonemura | |
| 5,508,170 A | 4/1996 | Butler et al. | |
| 5,851,836 A * | 12/1998 | Enomoto | G01N 33/86 |
| | | | 435/13 |
| 6,037,356 A | 3/2000 | Lu et al. | |
| 7,741,124 B2 | 6/2010 | Stief | |
| 2004/0077092 A1 * | 4/2004 | Wielinger | G01N 33/86 |
| | | | 436/10 |

FOREIGN PATENT DOCUMENTS

| | | |
|---|---|---|
| CN | 1504580 A | 6/2004 |
| DE | 195 49 118 A1 | 7/1997 |
| EP | 0 699 909 A2 | 3/1996 |
| EP | 0 699 909 A3 | 3/1996 |
| JP | 5 60763 | 3/1993 |
| JP | 08 15263 | 1/1996 |
| JP | 2994557 | 12/1999 |
| JP | 3074611 | 8/2000 |
| JP | 3330685 | 9/2002 |
| JP | 2003 344418 | 12/2003 |
| JP | 2004 191367 | 7/2004 |
| WO | WO 2006/063789 A1 | 6/2006 |

OTHER PUBLICATIONS

Extended European Search Report issued Jan. 7, 2013 in Patent Application No. 10777581.9.
Thomas W. Stief, et al., "Arginine Inhibits Hemostasis Activation", Thrombosis Research, Tarrytown, NY, ISSN: 0049-3848, DOI: 10.1016/S0049-3848 (01) 00368-1, XP-002249940A, vol. 104, No. 4, Nov. 15, 2001, pp. 265-274.
International Search Report issued on Jun. 15, 2010 in PCT/JP10/03401 filed May 20, 2010.
Office Action issued Sep. 29, 2013 in Chinese Patent Application No. 201080022099.5.

* cited by examiner

*Primary Examiner* — Ralph Gitomer
(74) *Attorney, Agent, or Firm* — Oblon, McClelland, Maier & Neustadt, L.L.P.

(57) ABSTRACT

A method for measuring blood coagulation, including: preparing a reaction solution including a plasma specimen, a blood coagulation activator, and at least one of aminoguanidine and an acid addition salt thereof; and measuring blood coagulation time by detecting a turbidity change in the reaction solution.

20 Claims, 5 Drawing Sheets

METHOD FOR MEASURING BLOOD COAGULATION

This application is a Continuation of U.S. application Ser. No. 14/153,739 filed on Jan. 13, 2014, which is a Divisional of U.S. application Ser. No. 13/321,732, filed on Nov. 21, 2011, which is a National Stage of application PCT/JP10/003401, filed on May 20, 2010.

FIELD OF THE INVENTION

The present invention relates to a reagent for measuring blood coagulability typified by a reagent for measuring fibrinogen; specifically relates to a blood coagulation time prolonging agent used in a blood coagulation activator-containing reagent and/or in a specimen diluent for measuring blood coagulability, and to a reagent for measuring blood coagulability using this blood coagulation time prolonging agent.

BACKGROUND OF THE INVENTION

Figure 1:
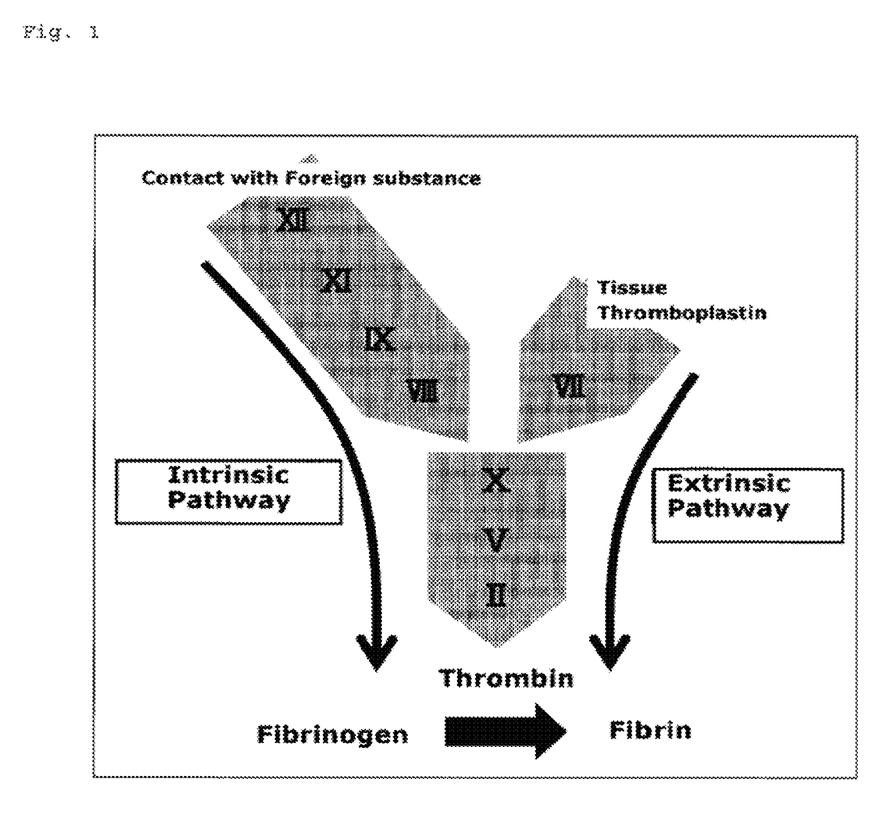
FIG. 1 is a view schematically showing a blood coagulation mechanism in a clinical examination.

A blood coagulation mechanism is broadly divided into two pathways in general. One is an intrinsic pathway, which is initiated by contact activation of blood coagulation factor XII with a foreign substance, and finally produces thrombin through multistep reactions, and the other is an extrinsic pathway, which is initiated by activation of blood coagulation factor X with blood coagulation factor VII and tissue thromboplastin, and produces thrombin in the same manner as described above (FIG. 1). In both of the pathways, coagulation eventually occurs by conversion of fibrinogen to fibrin through an action of produced thrombin. In order to clarify the presence or absence of abnormality or a cause of the abnormality in such blood coagulation mechanism, some blood coagulability tests using a blood coagulation activator are available and widely used in actual clinical examinations.

The blood coagulation activator and the blood coagulability tests using the same are as follows:
1) Blood Coagulability Tests Using Thrombin
   a fibrinogen measurement, an ATIII measurement, and a thrombin time measurement;
2) Blood Coagulability Tests Using Tissue Thromboplastin
   a prothrombin time measurement, an activity measurement of factor II, V, VII, or X using the prothrombin time measurement, and a measurement of complex factors (a thrombo test, a hepaplastin test, and the like); and
3) Blood Coagulability Tests Using Phospholipids
   a partial thromboplastin time measurement, an activated partial thromboplastin time measurement, an activity measurement of factor VIII, IX, XI, or XII, prekallikrein, or high molecular kininogen using the activated partial thromboplastin time measurement, a viper venom time measurement, a quantitative determination of factor X using the viper venom time measurement, a lupus anti-coagulant (LA) measurement using a diluted viper venom time measurement, a protein C activity measurement, and a thromboplastin generation test.

In any of the above-mentioned tests 1) to 3), a time from initiation of coagulation by mixing a reagent including a blood coagulation activator and the like with a specimen from a patient to final conversion of fibrinogen into fibrin to be deposited is measured.

Figure 2:
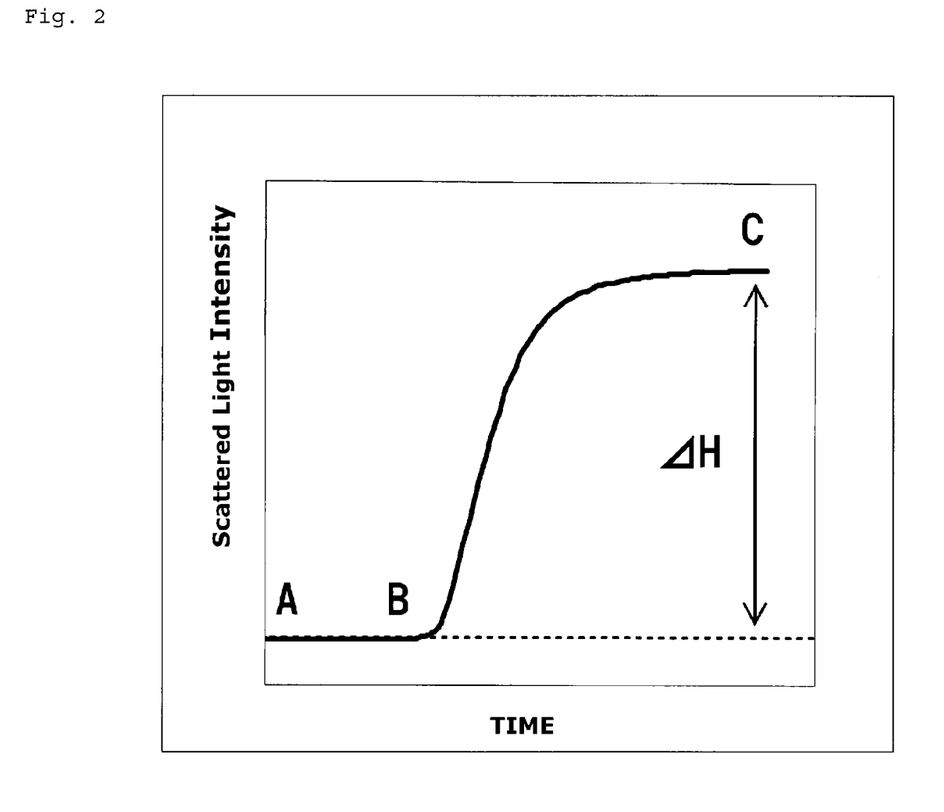
FIG. 2 is a graph showing one example of a change curve for scattered light intensity obtained by a scattered light detection method when blood coagulability is measured.

Methods of detecting coagulation in the blood coagulability test can be broadly divided into a mechanical detection method and an optical detection method. The mechanical detection method refers to a method including: monitoring by a magnetic force or the like a magnetic substance or the like loaded into a reaction solution; and detecting a decrease in mobility of the magnetic substance due to an increase in viscosity by coagulation. The optical detection method refers to a method including detecting white turbidity of a reaction solution due to coagulation as a change in transmitted light or scattered light, and is most widely used because the method is relatively simple. These are generally detected by an automated analyzer at present. One example of a change curve for scattered light intensity obtained in a scattered light detection method is shown in FIG. 2. In the figure, the point A indicates a point at which the coagulation is initiated by mixing a reagent including a blood coagulation activator, subsequently fibrin deposition is initiated through multistep reactions, and as a result, a change in scattered light intensity appears after the point B. Fibrinogen is in turn consumed and almost depleted in the reaction solution. Then, the scattered light intensity exhibits no change, the curve becomes flat as shown at the point C, and the coagulation is terminated. A coagulation time is calculated with known calculation parameters based on such change curve for the scattered light intensity (Patent document 1). Here, it is obvious that when a maximum of the change in scattered light intensity is defined as $\Delta H$, as the $\Delta H$ is larger, the coagulation is detected more sharply and more correct detection becomes possible. Thus, the reagent for measuring blood coagulability desirably has a property in which an optical change is largely displayed. However, when the change from the point A to the point C occurs in an extremely short period of time, it is impossible to measure a coagulation time with good accuracy. Thus, a substance for prolonging the coagulation time is generally added to adjust the coagulation time to a desired time. A blood coagulation time prolonging agent is exemplified by halide salts of alkali metals and alkali earth metals, including sodium chloride in Patent document 2, and by sodium propionate in Patent document 3. However, there has been a problem in that such conventional blood coagulation time prolonging agent also has a large negative effect of reducing $\Delta H$ in an addition dose-dependent manner.

For the purpose of solving the problems in those conventional methods, there is proposed a method including using a reagent supplemented with a high molecular material such as polyethylene glycol, polyvinyl alcohol or high molecular polysaccharide (Patent documents 4 and 5).

PRIOR ART

Patent Document

Patent Document 1: JP-08-15263 A
Patent Document 2: JP2994557 B2
Patent Document 3: JP3330685 B2
Patent Document 4: JP3074611 B2
Patent Document 5: JP05-60763 A

SUMMARY OF INVENTION

However, there are problems in that, in the method including adding a high molecular material to a reagent, the viscosity of the reagent itself is increased to reduce the accuracy of sampling the reagent with a pipette or a reagent probe, and in that a difference in turbidity between non-coagulated and coagulated solutions is not obtained sufficiently and consequently an optical change is not sufficiently enhanced.

Therefore, it is an object of the present invention to provide a reagent having a composition that prolongs a blood coagulation time to a desired time and enhances an optical change. This can contribute to enhancement of correctness in a blood coagulability test.

Thus, the inventors of the present invention have searched a blood coagulation time prolonging agent which enhances an optical change using various compounds, and have found that a guanidine compound having a specific structure or a salt thereof has not only an action of prolonging a blood coagulation time but also an action of enhancing an optical change upon coagulation, and the use thereof as an additive for a reagent for measuring blood coagulability al lows the blood coagulability to be measured correctly with high sensitivity, and have completed the present invention.

That is, the present invention provides a blood coagulation time prolonging agent, including, as an active ingredient, a guanidine compound represented by the following formula (1) or an acid addition salt thereof:

[Chem. 1]

(in the formula, $R^1$ represents a hydrogen atom, an amino group, or an alkyl group which may have a substituent).

Further, the present invention provides a blood coagulation activator-containing reagent or a specimen diluent for measuring blood coagulability, including the above-mentioned blood coagulation time prolonging agent.

In addition, the present invention provides a blood coagulation activator-containing reagent for measuring fibrinogen including thrombin as the blood coagulation activator or a specimen diluent for measuring fibrinogen, containing the above-mentioned blood coagulation time prolonging agent.

Further, in one aspect, the present invention provides a use of a guanidine compound represented by the following formula (1) or an acid addition salt thereof for prolonging a blood coagulation time:

[Chem. 2]

(in the formula, $R^1$ represents a hydrogen atom, an amino group, or an alkyl group which may have a substituent).

In one embodiment, the above-mentioned guanidine compound or acid addition salt thereof is used in combination with the blood coagulation activator. In another embodiment, the above-mentioned guanidine compound or acid addition salt thereof is used in combination with the specimen diluent for measuring blood coagulability.

Further, in one aspect, the present invention provides a method of prolonging a blood coagulation time, including adding to a plasma specimen a guanidine compound represented by the following formula (1) or an acid addition salt thereof:

[Chem. 3]

(in the formula, $R^1$ represents a hydrogen atom, an amino group, or an alkyl group which may have a substituent).

In one embodiment, the addition of the above-mentioned guanidine compound or acid addition salt thereof is carried out in combination with the specimen diluent for measuring blood coagulability. In another embodiment, the addition of the above-mentioned guanidine compound or acid addition salt thereof is carried out in combination with the blood coagulation activator.

Further, in one aspect, the present invention provides a method of measuring blood coagulability, including the steps of: preparing a reaction solution containing a plasma specimen, a blood coagulation activator, and the above-mentioned guanidine compound or acid addition salt thereof; and measuring a coagulation time of the reaction solution.

Further, in one aspect, the present invention provides a method of determining a fibrinogen concentration in the plasma specimen by comparing a measured value of the coagulation time using the plasma specimen with a measured value obtained by similarly measuring the coagulation time using a diluted standard solution in place of the plasma specimen.

Advantageous Effect of the Invention

When the blood coagulation time prolonging agent of the present invention is used, fibrinogen level, PT, and APTT for blood coagulability can be measured correctively because the optical change is enhanced.

DESCRIPTION OF PREFERRED EMBODIMENTS

A blood coagulation time prolonging agent of the present invention contains a compound represented by the formula (1) or a salt thereof as an active ingredient. In the formula (1), $R^1$ represents a hydrogen atom, an amino group, or an alkyl group which may have a substituent. Here, the alkyl group is preferably an alkyl group having 1 to 6 carbon atoms, particularly preferably an alkyl group having 2 to 5 carbon atoms. A group which may serve as a substituent of the alkyl group is exemplified by a carboxy group, an alkoxycarbonyl group, and an amino group. The alkyl group is preferably substituted with both of the carboxy group and the amino group or with both of the alkoxycarbonyl group and the amino group.

Specific examples of the compound represented by the formula (1) include guanidine, aminoguanidine, arginine, and an arginine alkyl ester. Of those, aminoguanidine is particularly preferred because an action of enhancing an optical change is large and the correct measurement can be performed. Further, examples of the acid addition salt of the compound of the formula (1) include a hydrochloride, a sulfate, a nitrate, a phosphate, and a sulfamate.

The blood coagulation time prolonging agent of the present invention has not only an action of prolonging a blood coagulation time but also an action of enhancing a turbidity change of a reaction solution in the measurement of blood coagulability. This indicates that a network of fibrin, which is a final product of blood coagulation, is more firmly formed. Therefore, the blood coagulation time prolonging agent of the present invention can be used in, for example, an optical detection method including directly detecting a turbidity change and a mechanical detection method including monitoring a formation state of a network of fibrin with a magnetic substance or the like. Of those, it is preferred to use the blood coagulation time prolonging agent in the optical detection method. Here, a method of detecting a scattered light amount and a method of detecting a transmitted light amount are available as the optical detection method. Of those, it is preferred to use the blood coagulation time prolonging agent in the method of detecting a scattered light amount.

A blood coagulability test to which the blood coagulation time prolonging agent of the present invention can be applied may be any test including measuring a time from the initiation of coagulation by mixing a reagent containing a blood coagulation activator and the like with a patient specimen to the final conversion of fibrinogen into fibrin to be deposited. Examples thereof include a fibrinogen measurement, an ATIII measurement, a thrombin time measurement, a prothrombin time measurement, an activity measurement of factor II, V, VII, or X using a prothrombin time, a measurement of complex factors (a thrombo test, a hepaplastin test, and the like), a partial thromboplastin time measurement, an activated partial thromboplastin time measurement, an activity measurement of factor VIII, IX, XI, or XII, prekallikrein, or high molecular kininogen using the activated partial thromboplastin time measurement, a viper venom time measurement, a quantitative determination of factor X using the viper venom time measurement, a lupus anti-coagulant (LA) measurement using a diluted viper venom time measurement, a protein C activity measurement, a thromboplastin generation test, and any other detection of abnormal coagulation.

In the measurement in the above-mentioned blood coagulability test, a time from the addition of a blood coagulation activator-containing reagent (e.g., a thrombin-containing reagent in the fibrinogen measurement) to a specimen to the deposition of fibrin is measured. The specimen is appropriately diluted with a specimen diluent if necessary. The blood coagulation time prolonging agent of the present invention has only to be contained in a measurement system. The blood coagulation time prolonging agent may be contained in the blood coagulation activator-containing reagent, or may be contained in the specimen diluent. That is, for example, in the fibrinogen measurement, the blood coagulation time prolonging agent of the present invention may be contained in the thrombin-containing reagent, or may be contained in the specimen diluent.

The above-mentioned blood coagulation activator-containing reagent has only to be one used for the above-mentioned blood coagulability test, and examples thereof include a thrombin-containing reagent, a tissue thromboplastin-containing reagent, and a phospholipid-containing reagent. Further, the above-mentioned specimen diluent has only to be one used for the above-mentioned blood coagulability test, and examples thereof include Good's buffers such as MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, and CHES, a citrate buffer, a phosphate buffer, an acetate buffer, an imidazole buffer, a barbital buffer, saline, and water.

The blood coagulation time prolonging agent of the present invention is preferably contained in the reaction solution so that a coagulation time which is measurable with high accuracy is obtained in the blood coagulability test. For example, in the fibrinogen measurement, the blood coagulation time prolonging agent is preferably contained in the reaction solution so that the coagulation time is 5 to 50 seconds, preferably 7 to 20 seconds, more preferably 9 to 15 seconds when normal plasma (concentration: about 300 mg/dL) is measured. When aminoguanidine is used as the blood coagulation time prolonging agent, the concentration of aminoguanidine in the reaction solution for the fibrinogen measurement, i.e., the concentration of aminoguanidine in a mixed solution of a specimen, a specimen diluent, and a thrombin-containing reagent is 10 to 500 mM, preferably 20 to 200 mM, more preferably 30 to 120 mM. When aminoguanidine is contained in the specimen diluent, the concentration of aminoguanidine in the specimen diluent is 10 to 900 mM, preferably 30 to 400 mM, more preferably 50 to 200 mM.

In the prothrombin time measurement, the blood coagulation time prolonging agent is preferably contained in the reaction solution so that the coagulation time is 9 to 60 seconds, preferably 9 to 30 seconds, more preferably 10 to 16 seconds when normal plasma (activity: about 100%) is measured. In the activated partial thromboplastin time measurement, the blood coagulation time prolonging agent is preferably contained in the reaction solution so that the coagulation time is 15 to 80 seconds, preferably 15 to 60 seconds, more preferably 20 to 50 seconds when normal plasma is measured. Also in the other blood coagulability tests, the blood coagulation time prolonging agent has to be contained in the reaction solution so that a coagulation time suitable for a measurement method is obtained.

In addition to the blood coagulation time prolonging agent of the present invention, known high molecular polysaccharides and synthetic polymers can be contained in the reagent for measuring blood coagulability including the specimen diluent and the blood coagulation activator-containing reagent used for the blood coagulability test.

Specific examples of the high molecular polysaccharides include dextran such as dextran 40, dextran 70, dextran 200000, or dextran 500000, and Ficoll, and the like. One kind of those high molecular polysaccharides may be used alone, or two or more kinds thereof may be used in combination. Those high molecular polysaccharides are each added in an amount so that the concentration in the reagent for measuring blood coagulability is suitably 0.01 to 10 W/V %, more preferably 0.1 to 5 W/V %.

Specific examples of the synthetic polymers include: polyvinyl alcohol such as polyvinyl alcohol 500, polyvinyl alcohol 1500, or polyvinyl alcohol 2000; polyethylene glycol such as polyethylene glycol 1500, polyethylene glycol 2000, polyethylene glycol 4000, polyethylene glycol 6000, polyethylene glycol 8000, or polyethylene glycol 20000; and polyvinylpyrrolidone. One kind of those synthetic polymers may be used alone, or two or more kinds thereof may be used in combination. The amount of each of those synthetic polymers to be added is not particularly limited, and the concentration thereof in the reagent for measuring blood coagulability is preferably 0.01 to 10 W/V, more preferably 0.1 to 5 W/V %.

The reagent for measuring blood coagulability can also contain a buffer, a calcium ion, an antagonist of an anticoagulant, and the like in addition to the blood coagulation time prolonging agent of the present invention.

As a specific example of the buffer, a buffer having a buffering ability in the range of pH 4 to 9 is appropriately selected and used. For example, the buffer can be selected from Good's buffers such as MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, and CHES, citric acid, phosphoric acid, acetic acid, imidazole, barbital, GTA, and the like, and one kind thereof may be used alone, or two or more kinds thereof may be used in combination. The amount of the buffer to be added is not particularly limited as long as the buffer has a buffering ability, and the concentration in the reagent for measuring blood coagulability is preferably 1 to 1,000 mM, more preferably 5 to 500 mM.

Water-soluble calcium compounds such as calcium chloride, calcium lactate, calcium gluconate, calcium glucuronate, and calcium tartrate are used as the calcium ion. One kind of those calcium compounds may be used alone, or two or more kinds thereof may be used in combination. The amount of each of the calcium compounds to be used is not particularly limited as long as the calcium compounds can help a coagulation reaction, and the concentration thereof in the reagent for measuring blood coagulability is preferably 5 mM to 100 mM, and more preferably 10 mM to 50 mM.

Protamine, polybrene (hexadimethrine bromide), and the like are used as the antagonist of the anticoagulant. One kind of those antagonists of the anticoagulant may be used alone, or two or more kinds thereof may be used in combination. The amount of the antagonist of the anticoagulant to be used is not particularly limited as long as the antagonist can sufficiently neutralize an anticoagulant such as heparin contained in specimen plasma, and the concentration in the reagent for measuring blood coagulability is preferably $10^{-5}$ to $10^{-2}$ W/V %, more preferably $5 \times 10^{-4}$ to $5 \times 10^{-3}$ W/V %.

Further, the reagent for measuring blood coagulability may be a liquid product, a frozen product, or a dried product, and the dried product is dissolved by adding purified water or a buffer.

Further, an appropriate preservative may be added to the reagent for measuring blood coagulability. The preservative can be selected from ciprofloxacin, propionic acid, sodium benzoate, sodium azide, ProClin 300, and the like, and one kind thereof may be used alone, or two or more kinds thereof may be used in combination. Further, salts such as sodium chloride, common stabilizers such as amino acids and sugars, and the like may be contained as needed.

The concentration described above is the concentration in the solution, and the concentration of the dried product or the like is the concentration when dissolved in water, a buffer, or the like before use.

The measurement of blood coagulability of the present invention can be conducted with a usual method. Taking the fibrinogen measurement as an example, a standard solution is diluted with a specimen diluent 5-fold, 10-fold, and 20-fold (a dilution rate can be adjusted appropriately). Next, two volumes of each diluted standard solution is warmed at 37° C. for 3 minutes, one volume of a thrombin reagent previously warmed at 37° C. is added, and a coagulation time is measured. Subsequently, a measured value of the each diluted standard solution is plotted on a graph. A plasma specimen is diluted with a specimen diluent 10-fold (a dilution rate can be adjusted appropriately), the diluted specimen is measured likewise, and the concentration can be obtained from the graph based on the obtained coagulation time.

EXAMPLES

Hereinafter, the present invention is described in more detail by way of examples, but the present invention is not limited to these examples.

Example 1

(1) Identification of Coagulation Time Prolonging Action

When a fibrinogen concentration in a plasma specimen is measured by a thrombin time method, in general, thrombin is added to plasma to measure a coagulation time, and the concentration is determined from a standard curve prepared using standard solutions having known fibrinogen concentrations. In the procedure, 90 μL of a specimen diluent are added to and mixed with 10 μL of specimen plasma, subsequently 50 μL of a thrombin-containing reagent are added as a blood coagulation activator-containing reagent, and a coagulation time is measured.

In this example, commercially available normal plasma (Coagtrol N, manufactured by Sysmex Corporation) as the plasma specimen, a Coagpia Fbg thrombin reagent (manufactured by Sekisui Medical Co., Ltd.) as the thrombin-containing reagent, and a full-automated blood coagulation time analyzer Coagrex 800 (manufactured by Sysmex Corporation) as a coagulation time measurement apparatus were used. This apparatus employs a scattered light detection method, and change data of scattered light intensity with time can also be obtained along with the coagulation time.

Figure 3:
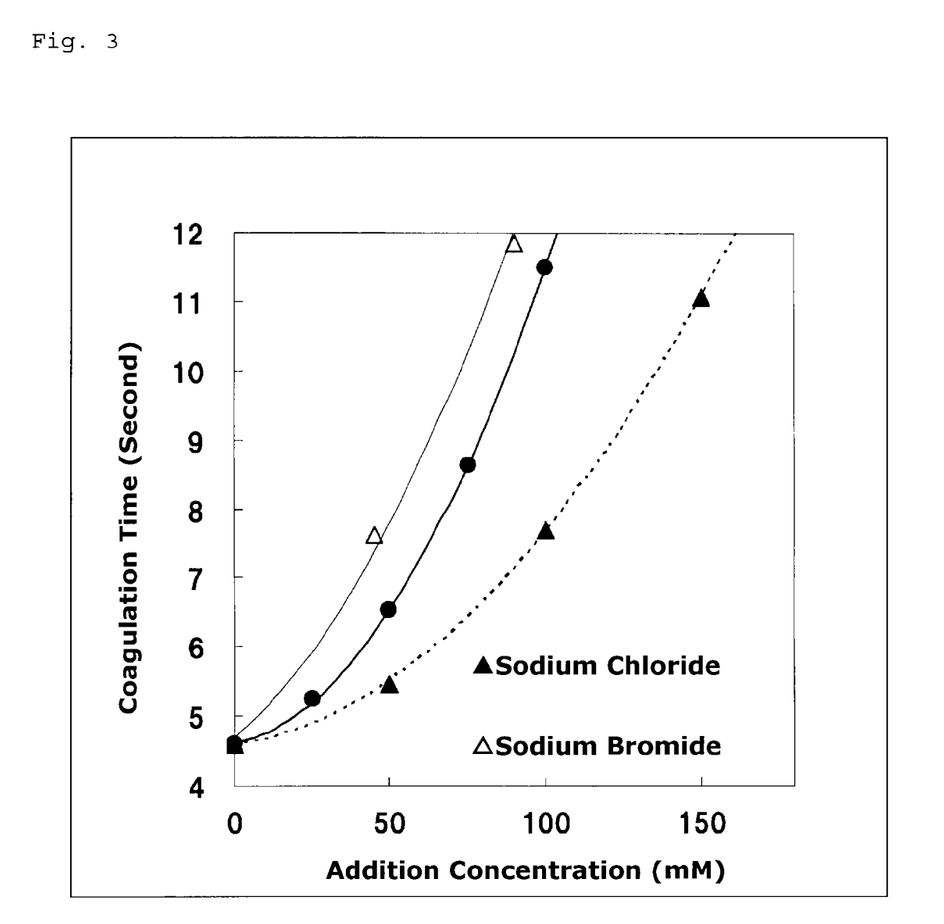
FIG. 3 is a graph showing a relationship between an addition amount and a coagulation time of each compound.

When an HEPES buffer (pH 7.5) was used as the specimen diluent, the commercially available normal plasma coagulated in several seconds (4.6 seconds). When aminoguanidine hydrochloride as the blood coagulation time prolonging agent was added to the HEPES buffer (pH 7.5), the coagulation time was prolonged in an addition concentration-dependent manner in the same manner as in conventional methods using sodium chloride and sodium bromide (results are shown in FIG. 3). That is, it is found that the present invention has the same coagulation time prolonging action as the conventional methods.

(2) Identification of Change in Light Intensity

Figure 4:
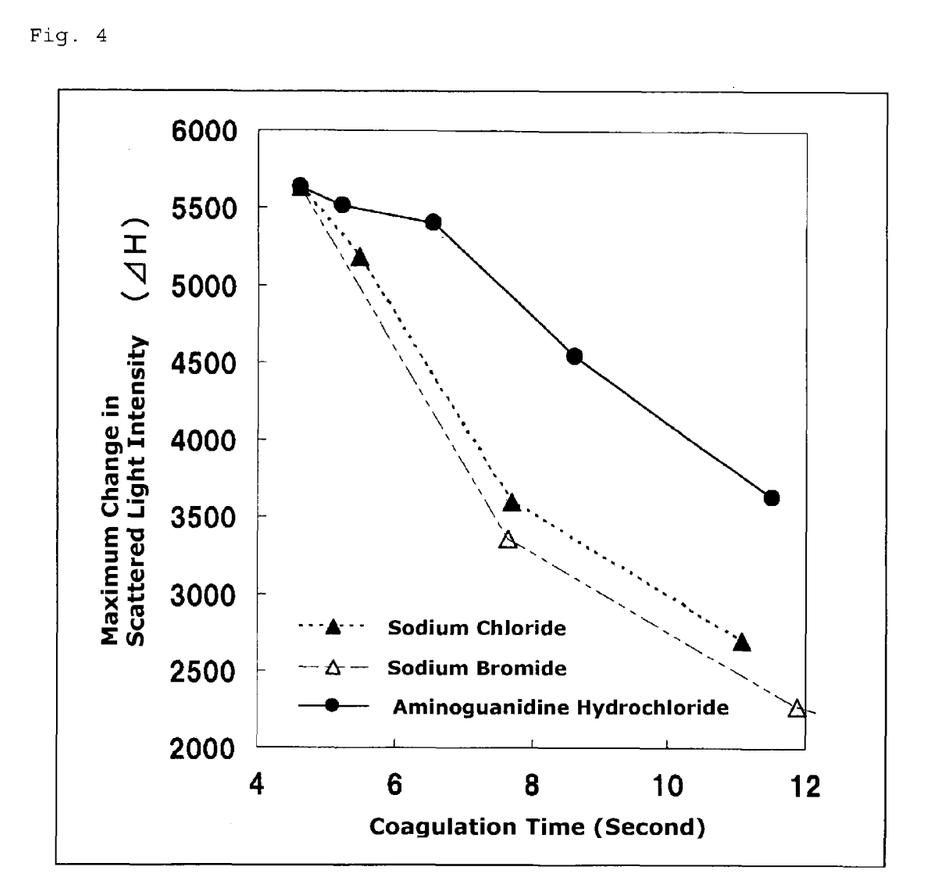
FIG. 4 is a graph showing a relationship between a coagulation time and a maximum of a change in scattered light intensity when the coagulation time is controlled by the addition of each compound.

A maximum of a change in scattered light intensity was calculated as ΔH, and its relationship with the coagulation time was shown in FIG. 4. ΔH was remarkably decreased along with the prolonged coagulation time in the conventional methods using sodium chloride and sodium bromide, while large ΔH was kept in the present invention. In other words, when the changes are compared in the similar coagulation time, the change in scattered light intensity is larger in the present invention than in the conventional methods, and it is found that the coagulation time can be measured more correctly in the present invention.

Example 2

Commercially available normal plasma was measured in the same manner as in Example 1 using the specimen diluent (HEPES buffer, pH 7.5) in which the amount of the blood coagulation time prolonging agent added was adjusted so as to obtain the similar coagulation time. The comparative results of the maximum of a change ΔH in scattered light intensity and of the simultaneous reproducibility of the measurements between in the conventional method and in the present invention were shown in Table 1. As compared with the conventional methods, it is found that the blood coagulation time prolonging agent of the present invention, i.e., arginine hydrochloride, arginine methyl ester, guanidine hydrochloride, guanidine phosphate, guanidine sulfamate, or aminoguanidine hydrochloride drastically enhances ΔH and further enhances the accuracy of the measurement (simultaneous reproducibility or the like). It was also found that aminoguanidine hydrochloride had a particularly excellent effect of improving the accuracy of the measurement (simultaneous reproducibility or the like).

TABLE 1

|  |  | ΔH | Coagulation time | Variation coefficient of measured values |
|---|---|---|---|---|
| Conventional method (1) | Sodium chloride: 145 mM | 2,348 | 10.7 | 4.47% |
| Conventional method (2) | Sodium bromide: 110 mM | 2,174 | 11.3 | * |
| Conventional method (3) | Potassium bromide: 105 mM | 2,127 | 11.4 | * |
| Conventional method (4) | Potassium chloride: 135 mM | 2,170 | 10.8 | * |
| Conventional method (5) | Lithium chloride: 135 mM | 2,305 | 10.8 | * |
| Method of the present invention (1) | Guanidine hydrochloride: 90 mM | 4,575 | 10.3 | 3.39% |
| Method of the present invention (2) | Guanidine phosphate: 30 mM | 4,217 | 10.4 | 2.36% |
| Method of the present invention (3) | Guanidine sulfamate: 55 mM | 5,167 | 11.2 | 3.29% |
| Method of the present invention (4) | Aminoguanidine hydrochloride: 90 mM | 3,480 | 9.7 | 1.94% |
| Method of the present invention (5) | Arginine hydrochloride: 55 mM | 3,529 | 10.3 | 2.77% |
| Method of the present invention (6) | Arginine methyl ester: 17 mM | 6,130 | 11.0 | 3.22% |

Single measurement was used in conventional methods (2) to (5) and ten times measurement was used in the others.
* Cannot be calculated Example 3

Figure 5:
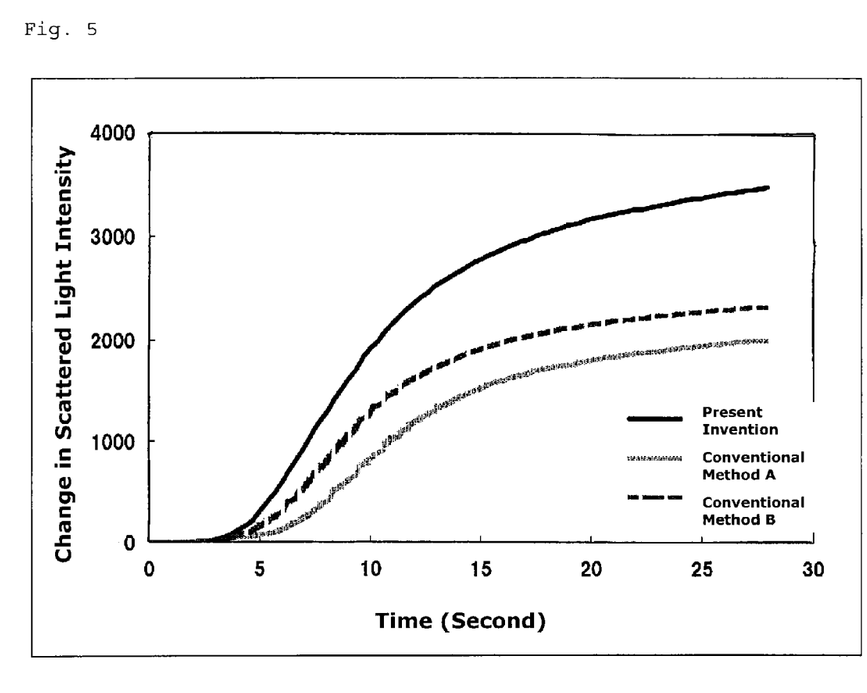
FIG. 5 is a graph showing change curves for scattered light intensity obtained by using reagents according to conventional methods and a reagent of the present invention.

A specimen diluent containing sodium chloride as the blood coagulation time prolonging agent was defined as a conventional method A and a specimen diluent further containing polyethylene glycol (molecular weight: 20000) (hereinafter, referred to as PEG 20000) as an enhancer of a change in light intensity in the conventional method A was defined as a conventional method B, and the specimen diluents were compared with a specimen diluent employing aminoguanidine hydrochloride (present invention) which served as both of the blood coagulation time prolonging agent and the enhancer of a change in light intensity. It should be noted that an HEPES buffer (pH 7.5) was used as a buffer in all of the cases. Further, the concentration of PEG 20000 to be added in the conventional method B was set to 0.1%, because a large amount of PEG 20000 could increase the viscosity of diluent and reduce the accuracy of sampling. The coagulation time of commercially available normal plasma was measured in the same manner as in Example 1 using each specimen diluent. As a result, a change curve for scattered light intensity as shown in FIG. 5 was obtained. Further, the coagulation time and ΔH were shown in Table 2. The change of the scattered light intensity in the conventional method B with the addition of PEG 20000 became larger than in the conventional method A without the addition. However, it is found that, by employing the present invention, the change of the scattered light intensity is more drastically enhanced and the coagulation time can be measured more correctly.

TABLE 2

|  | Conventional method A | Conventional method B | The present invention |
|---|---|---|---|
| Coagulation time prolonging agent | NaCl 150 mM | NaCl 150 mM | Aminoguanidine hydrochloride 90 mM |
| Enhancer of change in light intensity | — | PEG 20000 0.1% | |
| Coagulation time | 11.6 seconds | 10.4 seconds | 10.4 seconds |
| Change in light intensity ΔH | 2,194 | 2,244 | 3,444 |

Mean of three times measurement

The invention claimed is:

1. A method for measuring blood coagulation, comprising:
   preparing a reaction solution comprising a plasma specimen, a blood coagulation activator, and at least one of amino-guanidine and an acid addition salt thereof; and
   measuring blood coagulation time by detecting a turbidity change in the reaction solution.

2. The method according to claim 1, wherein the turbidity change is detected by a method of detecting a scattered light amount.

3. The method according to claim 1, wherein the amino-guanidine or an acid addition salt thereof is added to the reaction solution together with a specimen diluent for measuring blood coagulation.

4. The method according to claim 2, wherein the amino-guanidine or an acid addition salt thereof is added to the reaction solution together with a specimen diluent for measuring blood coagulation.

5. The method according to claim 3, wherein the specimen diluent is a specimen diluent for measuring fibrinogen.

6. The method according to claim 4, wherein the specimen diluent is a specimen diluent for measuring fibrinogen.

7. The method according to claim 1, wherein the blood coagulation activator is thrombin.

8. The method according to claim 5, wherein the blood coagulation activator is thrombin.

9. The method according to claim 6, wherein the blood coagulation activator is thrombin.

10. The method according to claim 5, wherein the measuring of blood coagulation time is performed by a fibrinogen measurement method.

11. The method according to claim 6, wherein the measuring of blood coagulation time is performed by a fibrinogen measurement method.

12. The method according to claim 7, wherein the measuring of blood coagulation time is performed by a fibrinogen measurement method.

13. The method according to claim 9, wherein the measuring of blood coagulation time is performed by a fibrinogen measurement method.

14. The method according to claim 9, wherein the measuring of blood coagulation time is performed by a fibrinogen measurement method.

15. The method according to claim 1, wherein the reaction solution comprises amino-guanidine.

16. The method according to claim 1, wherein the reaction solution comprises an acid addition salt of amino-guanidine.

17. The method according to claim 1, wherein the acid addition salt of amino-guanidine is at least one salt selected from the group consisting of a hydrochloride salt of amino-guanidine, a sulfate salt of amino-guanidine, a nitrate salt of amino-guanidine, a phosphate salt of amino-guanidine, and a sulfamate salt of amino-guanidine.

18. The method according to claim 1, wherein the at least one of amino-guanidine and an acid addition salt thereof is amino-guanidine hydrochloride.

19. The method according to claim 1, wherein the amino-guanidine has the formula where $R^1$ is an amino group.

20. The method according to claim 17, wherein the amino-guanidine has the formula where $R^1$ is an amino group.

* * * * *